(12) United States Patent
Iparraguirre et al.

(10) Patent No.: US 8,641,687 B2
(45) Date of Patent: Feb. 4, 2014

(54) VAGINAL HYGIENE SYSTEM

(75) Inventors: Jose I Iparraguirre, Miami, FL (US); Craig Lichtblau, Jupiter, FL (US)

(73) Assignee: JICL IP Company, LLC, North Palm Beach, FL (US)

( * ) Notice: Subject to any disclaimer, the term of this patent is extended or adjusted under 35 U.S.C. 154(b) by 20 days.

(21) Appl. No.: 13/542,879

(22) Filed: Jul. 6, 2012

(65) Prior Publication Data

US 2014/0012191 A1   Jan. 9, 2014

(51) Int. Cl.
   *A61M 31/00*   (2006.01)

(52) U.S. Cl.
   USPC .......................................................... 604/279

(58) Field of Classification Search
   USPC ....................... 604/279, 82, 87, 89
   See application file for complete search history.

(56) References Cited

U.S. PATENT DOCUMENTS

| | | |
|---|---|---|
| 2,087,780 A | 7/1937 | Powell |
| 2,195,945 A | 4/1940 | Szasz |
| 2,591,371 A | 4/1952 | Nimmo |
| 2,664,893 A | 1/1954 | Kempel |
| 2,887,109 A | 5/1959 | Barrington |
| 3,354,883 A | 11/1967 | Southerland |
| 3,401,695 A | 9/1968 | Rosenberg |
| 3,653,377 A | 4/1972 | Rebold |
| 3,693,783 A | 9/1972 | Hart |
| 3,726,276 A | 4/1973 | Schumann |
| 3,768,475 A | 10/1973 | Osborne |
| 3,802,434 A | 4/1974 | Brooks |
| 3,892,311 A | 7/1975 | Sneider |
| 3,965,899 A | 6/1976 | Murray |
| 4,014,332 A | 3/1977 | Sneider |
| 4,057,060 A | 11/1977 | Roth |
| 4,180,072 A | 12/1979 | Sneider |
| 4,223,814 A | 9/1980 | Sneider |
| 4,262,669 A | 4/1981 | Sneider |
| 4,318,403 A | 3/1982 | Sneider |
| 4,383,531 A | 5/1983 | Panagiotopulos |
| 4,405,306 A | 9/1983 | Pritchard |
| 4,510,630 A | 4/1985 | Osgood |
| 4,709,705 A | 12/1987 | Truglio |
| 4,850,965 A | 7/1989 | Zinopoulos |

(Continued)

FOREIGN PATENT DOCUMENTS

| | | |
|---|---|---|
| EP | 698399 | 7/1995 |
| JP | 09182786 | 7/1997 |

OTHER PUBLICATIONS

Owen MK, ClenneyTL. Management of vaginitis. Am Fam Physician 2004;70:2125-2132.

(Continued)

*Primary Examiner* — Aarti B Berdichevsky

(74) *Attorney, Agent, or Firm* — Ferris H. Lander Inc.

(57) ABSTRACT

A device and kit are described for mixing and instillation of a two-part chemical system within a body cavity, under pressure. More particularly, a vaginal hygiene system is illustrated utilizing a two-part chemical system effective for achieving stasis of the vaginal flora, whereby bacterial vaginosis is effectively mitigated, thereby eliminating undesirable vaginal discharge and discomfort. In one embodiment a kit is described including a highly portable dispenser having separate and distinct reservoirs which segregate the two-part chemical system until the desired time of use, and further include a combination applicator nozzle and blending manifold, wherein activation of the device results in the fluidic coupling of the chemical reservoirs, and provides immediate intermixing of the two-part chemical system concomitant with pressurized expulsion through an imperforate nozzle into the vaginal canal.

15 Claims, 10 Drawing Sheets

(56) References Cited

U.S. PATENT DOCUMENTS

| | | |
|---|---|---|
| D343,447 S | 1/1994 | Thaler |
| 5,383,579 A | 1/1995 | Lanfranconi |
| D358,872 S | 5/1995 | Fonda |
| 5,785,688 A | 7/1998 | Joshi |
| 5,845,814 A | 12/1998 | Nobbio |
| 5,853,388 A | 12/1998 | Semel |
| 5,858,010 A | 1/1999 | Berry |
| 6,190,366 B1 | 2/2001 | Tani |
| 6,199,726 B1 | 3/2001 | Cardwell, III |
| 6,752,792 B1 | 6/2004 | Robertson |
| D568,465 S | 5/2008 | Pierre |
| 7,789,854 B2 | 9/2010 | Talamonti |
| 7,815,075 B2 | 10/2010 | Simkins |
| 7,959,597 B2 | 6/2011 | Baker |
| 2005/0119621 A1 | 6/2005 | Bang |
| 2007/0062982 A1 | 3/2007 | Blum |
| 2008/0154291 A1 | 6/2008 | Bosma |

OTHER PUBLICATIONS

Klebanoff, MA et al., Vulvovaginal symptoms in women with bacterial vaginosis. Obstet Gynecol 2004;104:267-272.

Priestly, CJ et al., What is normal vaginal flora?. Genitourin Med 1997;73:23-28.

Sobel, JD, What's new in bacterial vaginosis and trichomonas ? Infec Dis Clin N Am 2005;387-406.

Allsworth,JE et al., Prevalence of bacterial vaginosis: 2001-2004 National Health and Nutritional Examination Survey Data. Obstet Gynecol. Jan. 2007; 109(1):114-120.

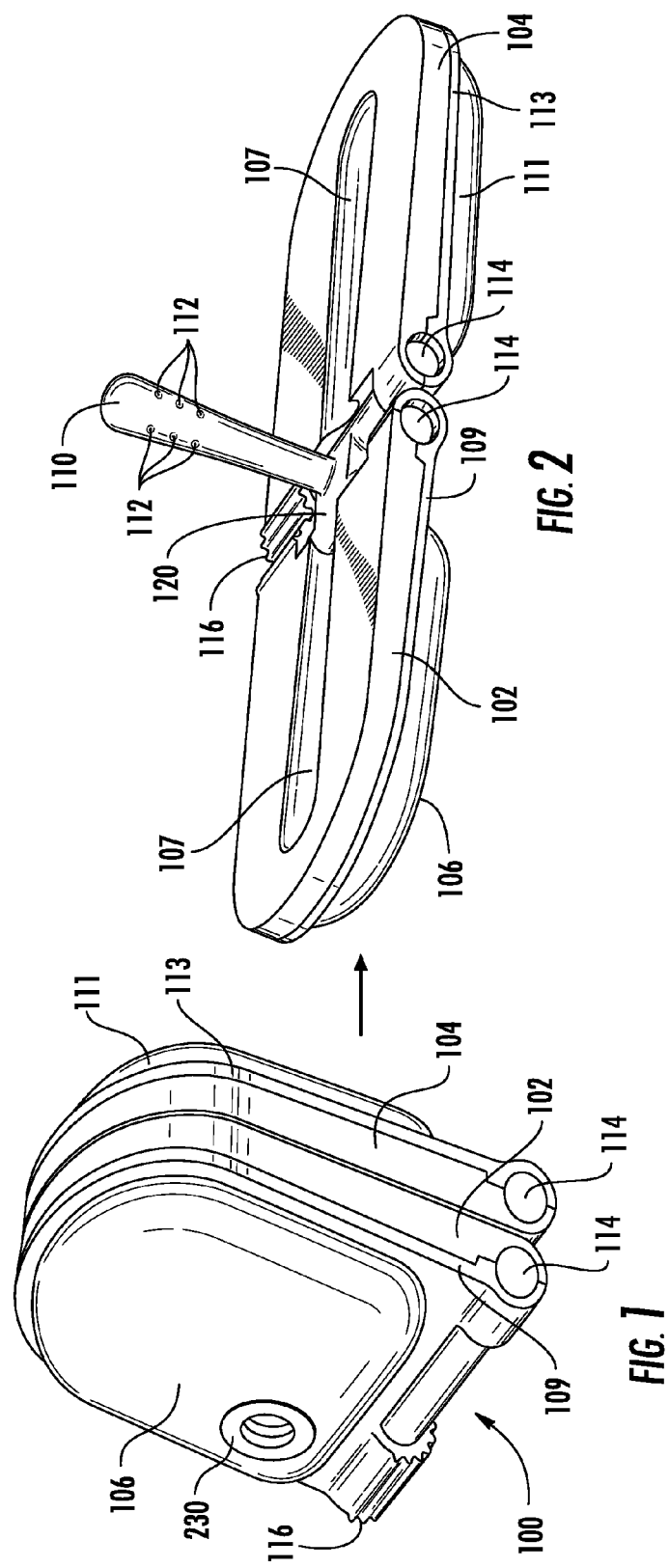

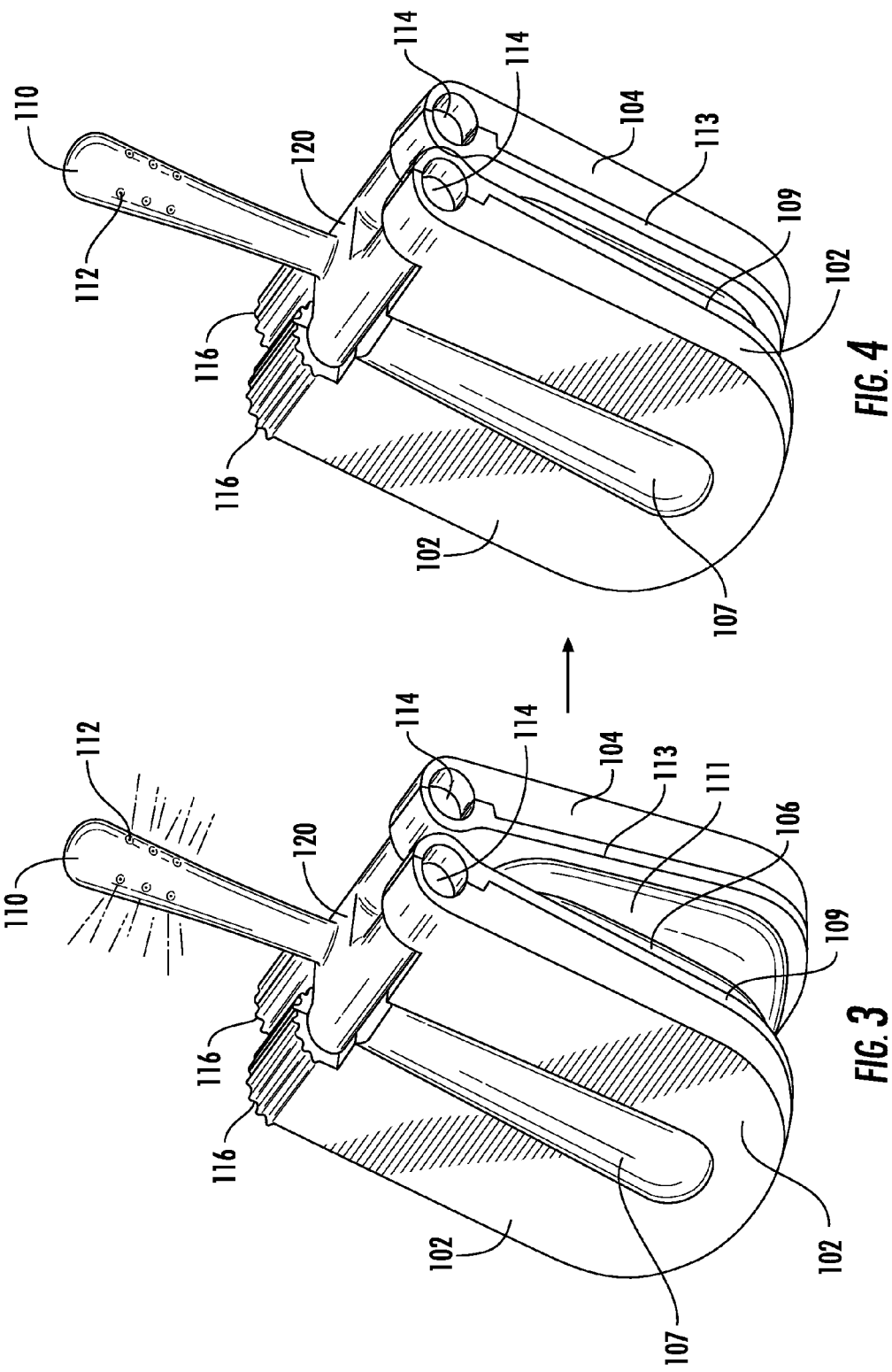

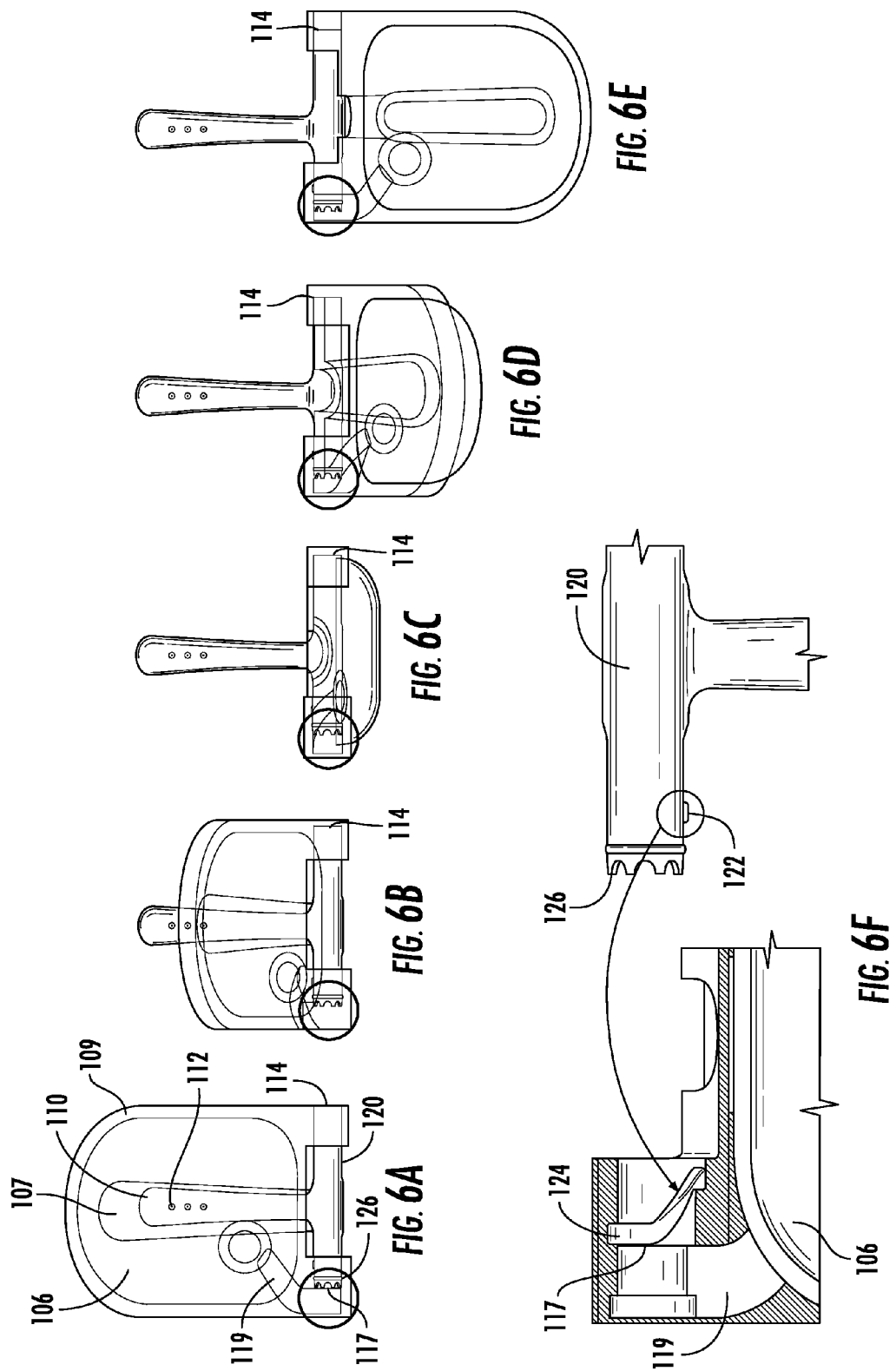

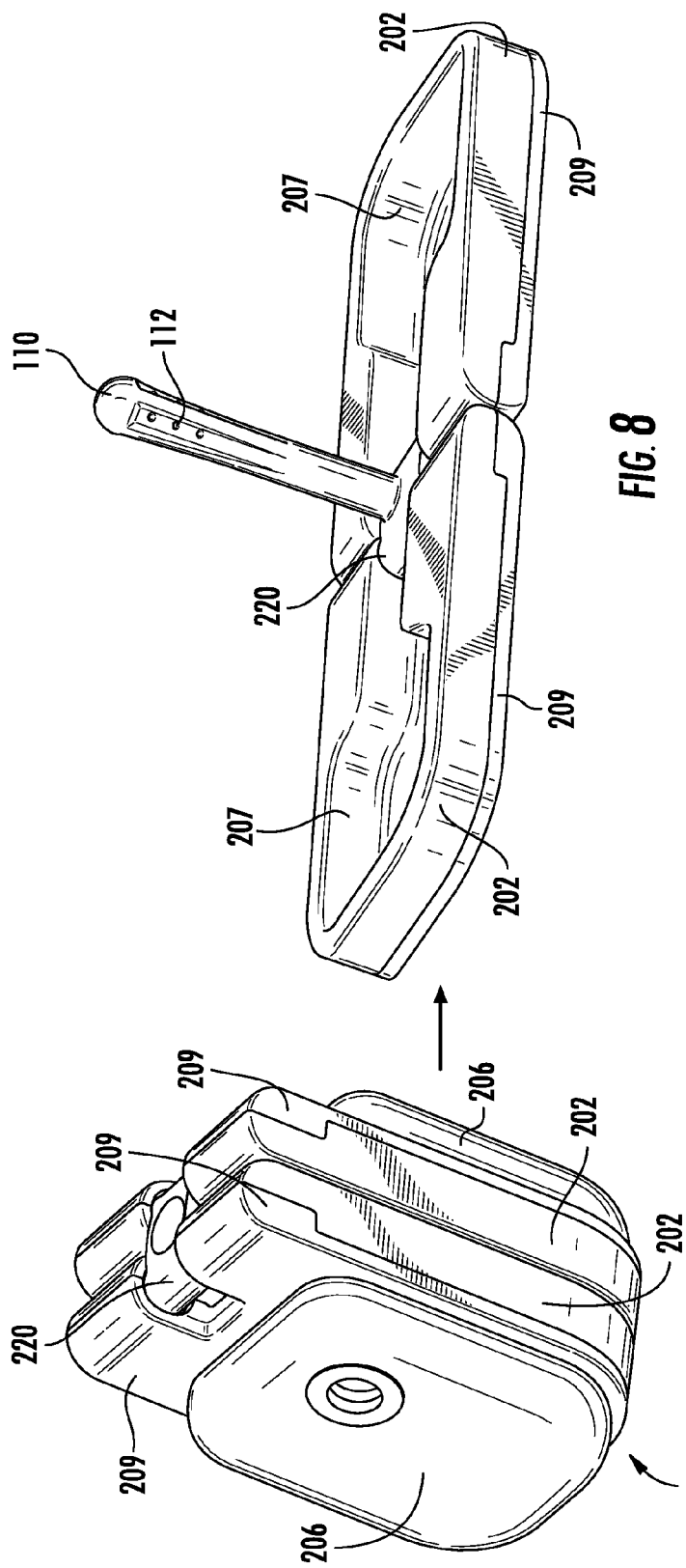

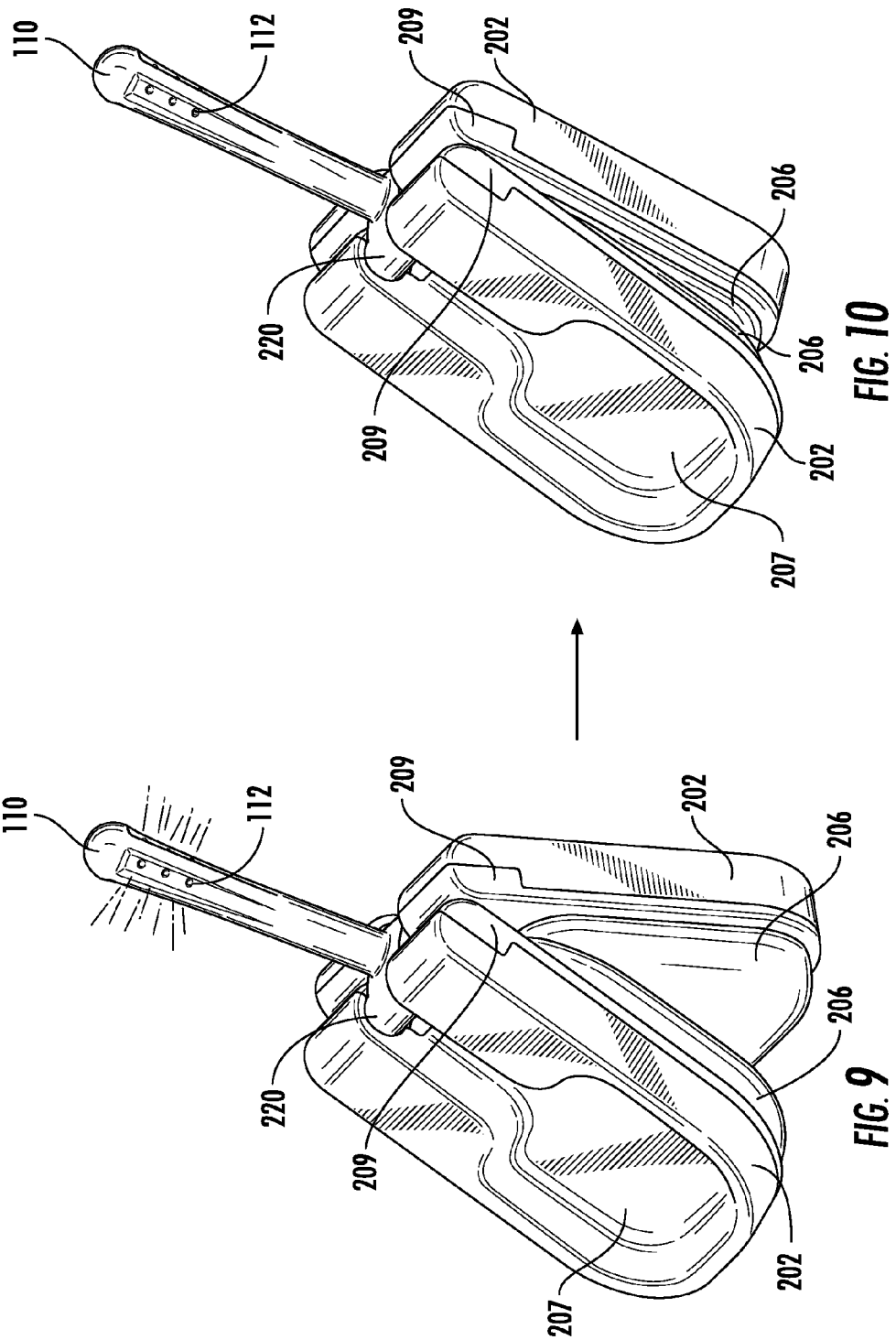

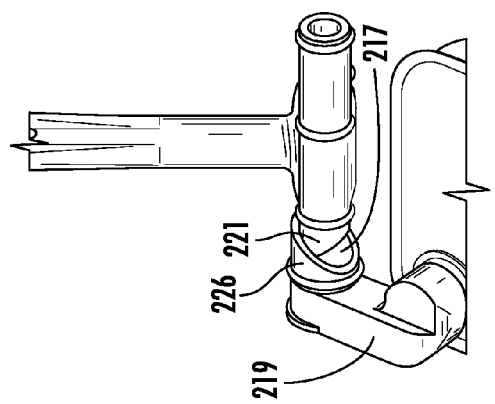
FIG. 13A    FIG. 13B
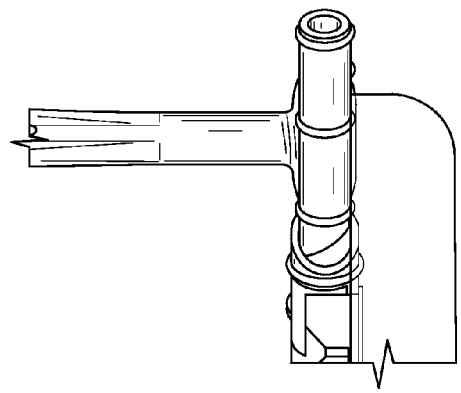
FIG. 13C    FIG. 13D
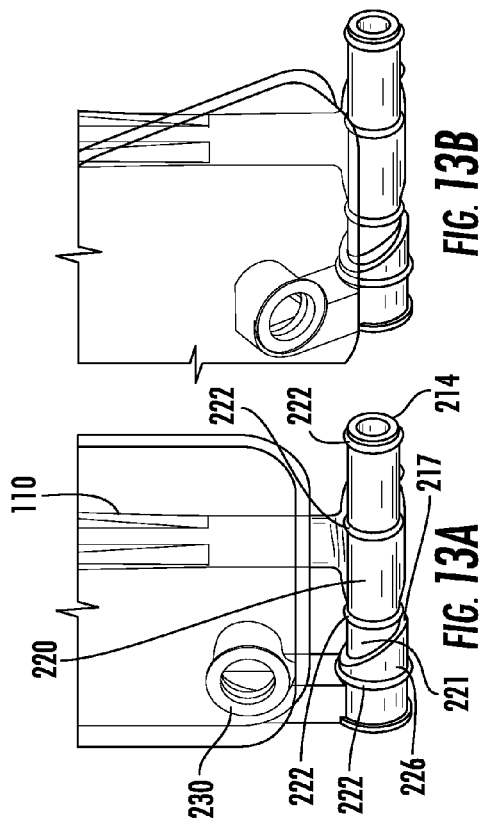
FIG. 13E    FIG. 13F    FIG. 13G    FIG. 13H
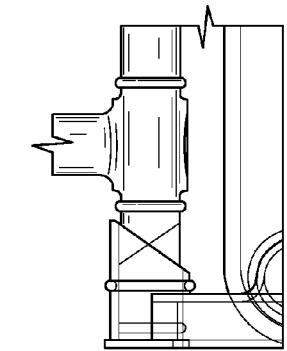
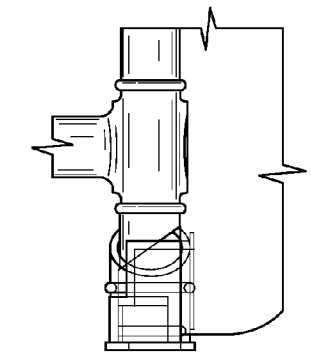
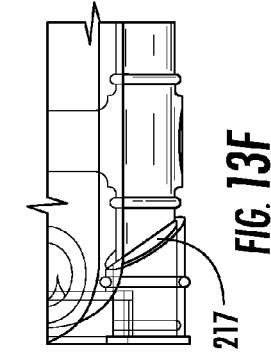
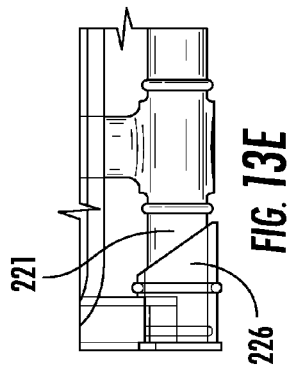

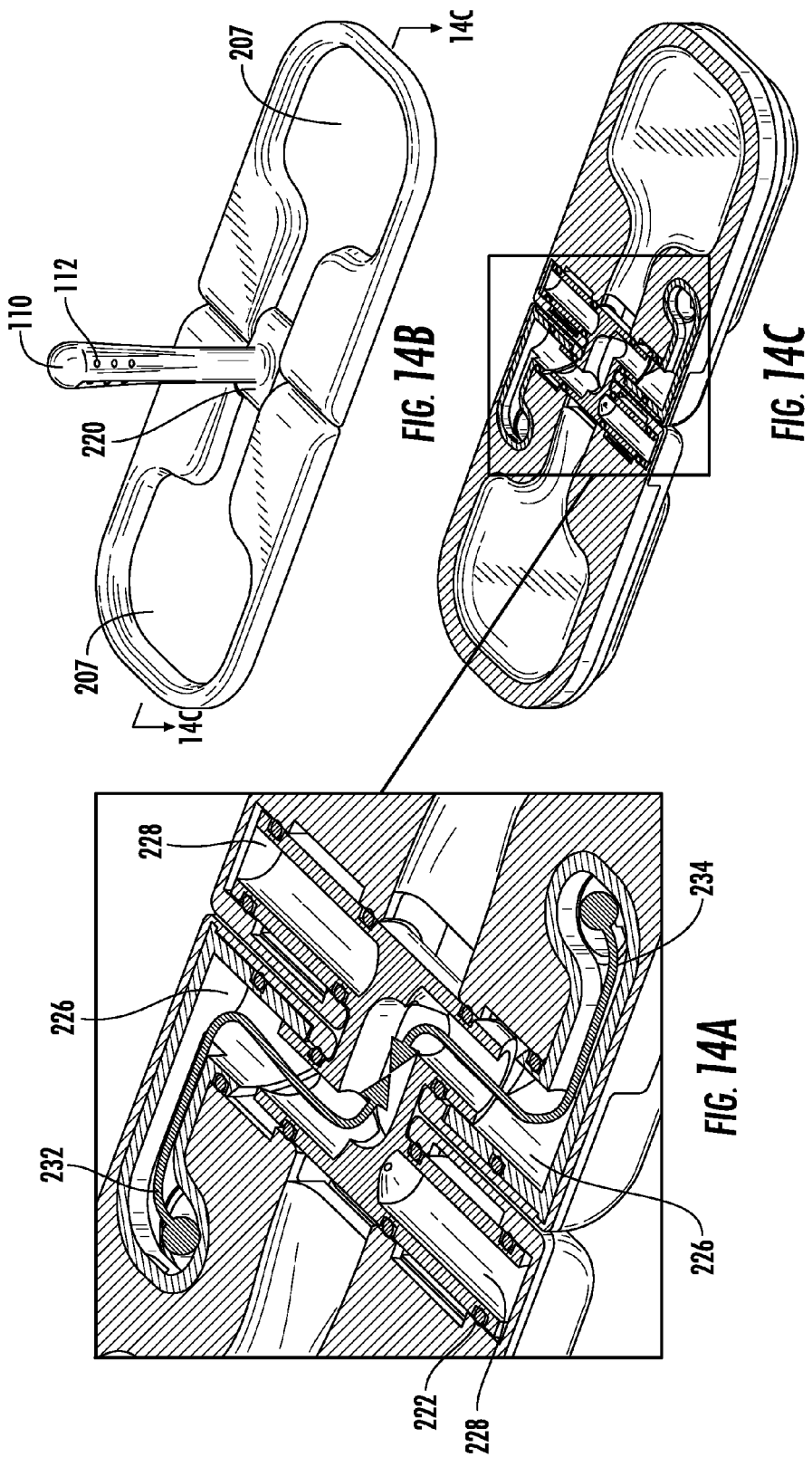

VAGINAL HYGIENE SYSTEM

FIELD OF THE INVENTION

This invention generally relates to a device and kit for mixing and instillation of a two-part chemical system within a body cavity, under pressure. More particularly, the invention relates to a vaginal hygiene system, particularly to a two-part chemical system effective for achieving stasis of the vaginal flora, whereby bacterial vaginosis is effectively mitigated, thereby eliminating undesirable vaginal discharge and discomfort. The invention most particularly relates to a kit including a highly portable dispenser having separate and distinct reservoirs which segregate the two-part chemical system until the desired time of use, and further including a combination applicator nozzle and blending manifold, wherein activation of the device results in the fluidic coupling of the chemical reservoirs, and provides immediate intermixing of the two-part chemical system concomitant with pressurized expulsion through an imperforate nozzle into the vaginal canal.

BACKGROUND OF THE INVENTION

The vagina is a dynamic ecosystem that normally contains approximately $10^9$ bacterial colony-forming units per gram of vaginal fluid. The normal vaginal fluid is clear to white, odorless, and of high viscosity. Normal bacterial flora is dominated by *lactobacilli*, however, a variety of other organisms, including some potential pathogens, are also present at lower concentrations.

Normally, the action of *Lactobacilli* converts glycogen to lactic acid, whereby the lactic acid provides a physiologic lowering of pH. The normal vagina of a woman of reproductive age has a pH of 3.8 to 4.2. This lower pH provides a protection by making the vaginal environment less hospitable to certain pathogens, specifically certain yeast and other bacteria.

Some *lactobacilli* also produce hydrogen peroxide ($H_2O_2$), which has microbicidal properties that can kill bacteria and viruses.

When the normal balance of microorganisms is disrupted, bacterial vaginosis can occur, leading to vaginal discomfort ranging from itching to a burning sensation along with vaginal discharge. Vaginal discharge is one of the most common conditions for which women seek medical care. Approximately 10 million office visits each year are attributed to vaginal discharge complaints.

The present inventors have discovered that a two-part chemical system, preferably formed from acetic acid and hydrogen peroxide, can aid in achieving stasis of the vaginal flora, returning the vaginal canal to its normal pH and mitigating the effects of bacterial vaginosis.

One problem with this treatment is that the chemicals must be admixed just prior to their application to the vaginal canal in order to maintain maximum effectiveness. Although it would be ideal to instill such a solution as desired, having to carry around the individual components of the chemical system in separate portions, mixing them and then inserting the blended components into the vaginal canal is cumbersome and inconvenient. Therefore, such treatments have generally been instilled in the home or at a doctor's office.

If a portable device could be provided which enabled easy transport of such a chemical system, and further provided for ease of intermixing and subsequent insertion into the vaginal canal, a long felt need would be realized.

DESCRIPTION OF THE PRIOR ART

U.S. Pat. No. 7,959,597, entitled "Irrigation And Aspiration Device And Method" to Baker et al., discloses an irrigation and aspiration system. The system can be configured to aspirate and irrigate alone, sequentially or concurrently. The system can be configured to aspirate and irrigate the nasal cavity. The system can be manually controlled. The system can have removable and easily cleanable reservoirs for aspirant and irrigant.

U.S. Pat. No. 7,789,854, entitled "Medical Treatment Kit And Methods Of Use Thereof" to Talamonti, discloses a medical treatment kit and methods of use thereof. The kit includes a container, two or more chambers within the container, an antiseptic agent disposed in one of the chambers, a cleansing agent disposed in a separate chamber and an applicator. The agents are not contacted until immediate use of the kit is required. The medical treatment kit is used to administer an antiseptic shampoo or other medical composition to a patient with an open wound or injury. The kit is designed to be simple to use in an emergency situation. The kit is also designed to deliver medical compositions that are at the peak of potency.

This device fails to teach a kit including a highly portable dispenser having separate and distinct reservoirs to segregate the two-part chemical system until the desired time of use, and a combination applicator nozzle and blending manifold, wherein activation of the device fluidically couples the chemical reservoirs, and provides immediate intermixing of the two-part chemical system concomitant with a pressurized expulsion of the now blended chemical system within a body cavity.

U.S. Pat. No. 6,537,260 entitled "Substance Applicator" to Lamb, is directed toward an applicator for applying or delivering a substance into a body cavity includes a deformable reservoir for receiving and expelling the substance. The reservoir has an inlet spaced from an outlet, the inlet being configured to be connected to a container containing the substance. Valve means is positioned in the inlet to inhibit flow of the substance into the body cavity is in flow communication with the reservoir through the outlet of the reservoir.

U.S. Pat. No. 6,190,366, entitled "Portable, Locally Washing Hygienic Device" to Tani, is directed toward a portable, locally washing hygienic device having a water container of a flexible synthetic resin film member, a water supply tube mounted on the water container and acting as a water passage, a spray nozzle mounted on an upper portion of the water supply tube, and a valve assembly interposed between the spray nozzle and the water supply tube, in which a lower portion of the water supply tube located within the water container is joined together through a connecting member with an inner surface portion of the water container by thermally fusing or otherwise.

U.S. Pat. No. 5,858,010, entitled "Personal Hygiene Washing System" to Berry, teaches a personal hygienic washing system for douching the external pelvic area as well as for use internally. The inventive device includes a contoured cleaning member having a plurality of irrigation holes, a squeezable bottle and means for attaching the cleaning member to the squeezable bottle.

U.S. Pat. No. 5,845,814, entitled "Bottle For Separately Preserving Substances And Subsequently Dispensing Their Mixture Dropwise" to Nobbio, teaches a bottle whose purpose is to enable substances to be separately preserved and the mixture of said substances to be subsequently dispensed dropwise only under the control of the operator. The bottle comprises a container and a closure element applicable to its mouth. The closure element comprises a pump provided with a dispensing orifice and accessible to the users fingers through at least one opening in the cap. A separator element is housed in the interior of said pump, and is removable for squeezing the pump.

U.S. Pat. No. 5,383,579, entitled "Container For Containing Two Flowable Materials In Separated Compartments, But Permitting The Two Materials To Be Mixed For Dispensing, Before The Container Is Opened" to Lanfranconi et al., discloses a device for containing and dispensing a flowable material, for once-only use includes a container, to the delivery mouth of which a cannula can be fitted. The container includes a body and a sealed chamber, which are separated by a stopper, which is neutralizable by bending or compressing a deformable portion of the body relative to the sealed chamber.

U.S. Pat. No. 4,405,306, entitled "Medicated Disposable Douche Product" to Pritchard et al., discloses a douche product which comprises a bottle filled with a douching liquid, a reservoir in the bottle containing a liquid to be mixed with the douching liquid and a nozzle attached to the bottle for dispensing the contents of the bottle, the nozzle and the reservoir having cooperating devices so that the reservoir may be opened to permit the contents thereof to drain into the bottle when the nozzle is moved relative to the bottle.

U.S. Pat. No. 4,318,403, entitled "Foldable Nozzle Syringe" to Sneider, is directed toward a syringe for vaginal douche, swab, or the like applications. A flexible fluid container has an elongated tubular discharge nozzle molded integrally therewith as an extension of one end of the container, and at least the juncture of the nozzle and the container is flexible to facilitate bending and folding of the nozzle to a position alongside the container. An elongated slot is formed on the side of the container for receiving the nozzle when in its folded position substantially within the outer confines of the container. Detent protrusions along opposite edges of the slot releasably retain the nozzle in its folded position within the slot. The entire foldable nozzle syringe is formed as an integral molded and prefilled construction, and an integral frangible cap is provided on the distal end of the nozzle, the latter being threaded for attachable association with a douche, swab or other attachment.

U.S. Pat. No. 4,262,669, entitled "Accordion-style Syringes, Douches And Attachments Therefore" to Sneider, is drawn toward improvements in accordion-style containers used with syringes, douches and the like. These improvements pertain to both prefilled, disposable, reusable syringe and douche containers and accessories used therewith. Among the novel constructions of containers is included a barium enema container in which the side is made with a flattened portion to provide a positive rest position on a flat surface such as a floor with the outlet of the container in a positive elevated condition. A contoured end on a prefilled, disposable douche container is adapted to act as a plug or dam against an unwanted escape of fluid. A sliding plug of like contour may be carried on tubing, which is used with a douche or enema container. Among the accessories is a nozzle having outwardly directed jet outlets adjacent and to the rear of a parabolic cone. Molded nozzles having large transverse outlets are also shown as is a stand and container providing an additional barium enema supply.

U.S. Pat. No. 4,223,814, entitled "Expandable Syringe And Sprinkler Cap Therefore, to Sneider, teaches an expandable syringe comprising a bag having an opening through which liquid may pass. A closed end tubular view stem projects outwardly from the bag opening and has an orifice in the side thereof in fluid communication with the interior of the bag. A nozzle has a female coupler sized to be movably mounted about the valve stem. The nozzle coupler has a valve seat against which the valve stem closed end may operationally engage in controlling the flow of liquid between the bag and nozzle. The bag may comprise a corrugated container or a shell having first and second openings and flexible pocket mounted to the shell sealing the first opening and sized for maneuver into and out of the shell through the first opening to displace liquid out of the shell. A nozzle or sprinkler cap may be detachably mounted to the shell over the second opening. Upon detachment of the nozzle or cap from the shell liquid may be introduced into the shell through the second opening thereby forcing the pocket to a position outside the shell. The nozzle or sprinkler cap may then be attached and the pocket squeezed into the shell thereby forcing the liquid out of the shell and nozzle. The sprinkler cap comprises a tubular member and an apertured sprinkler plate mounted therein having an elongated plate ledge. An articulated cover is joined to the tubular member at a joint aside the sprinkler plate. The cover has two sections hinged together along an elongated hinge parallel the plate ledge between the ledge and corner joint.

U.S. Pat. No. 4,057,060, entitled "Disposable Medicinal Application Apparatus" to Roth, teaches a disposable medicinal application apparatus for use in the administration of a medicinal fluid. The device comprises a sealed flexible bag means at least partially filled with a quantity of the fluid to be applied. The apparatus has a neck piece freely enclosed within the sealed bag means, the neck piece being manipulable against the interior surface of a portion of the bag means and the bag wall being stretched over the neck piece. A separate applicator member has a passage in communication with discharge means. Cooperative locking and lockable means are formed on the applicator member and the neck piece, respectively, to allow the applicator member to be snap-fitted and locked to the neck piece, with the bore of the neck piece and the passage of the applicator member in alignment. A portion of the bag wall is compressed between the exterior surface of the neck piece and the interior surface of the applicator member to form a fluid tight seal there between. A portion of the applicator member comprises means for puncturing the bag wall to allow egress of the medicinal fluid through the aligned bore and passage of the cooperatively locked neck piece and applicator member.

U.S. Pat. No. 4,014,332, entitled "Disposable Syringes" to Sneider, teaches a liquid filled sealable flexible bag having a manipulative discharge tube or nozzle. As a vaginal douche the discharge tube is removably equipped with a vaginal fitting which telescopically engages the tube. Positive closing means of the discharge tube is provided. The filled and plugged bag, complete with vaginal fitting, may be encased in a sealed envelope which in turn is conveniently accommodated in a purse-like flexible case. To use the device after breaking the sealed envelope, the vaginal fitting is removed and the douche is ready for administration. In addition to the syringe there is disclosed an enema bag and including manipulative valve shutoff means.

U.S. Pat. No. 3,965,899, entitled "Hygienic Douche System" to Murray et al., teaches a hygienic douche apparatus including a nozzle for insertion into a vaginal passage and a cooperating fluid holding container. The container includes a separate compartment therein to hold a compound, which is soluble in a fluid such as water and, when dissolved, forms a hygienic douching fluid. The compound includes an ingredient, which reacts with water to evolve a gas to pressurize the container and dispel the hygienic douching fluid through the nozzle. The compartment includes means operable from outside the container to initiate contact between the liquid and the compound. The apparatus is also adaptable to be used with an enema-type nozzle to provide a convenient readily dispensable enema and with a bidet nozzle to provide a convenient bidet apparatus.

U.S. Pat. No. 3,892,311, entitled "Disposable Syringe Kit" to Sneider, relates to a disposable syringe kit in which a nozzle portion is detachably attached to an end closure member having a tubular portion and a cap portion. A flexible bag is packed in collapsed form and has an open or openable end that is sized for mounting on the tubular portion. In disassembled array in the kit, the syringe parts may be packaged in a decorative case, carton, plastic bag, or the like for shipping and/or dispensing, as by means of a vending machine. After assembly and use, the complete unit or merely the bag component may be disposed of, as desired.

U.S. Pat. No. 3,802,434, entitled "Disposable Syringe" to Brooks, is directed toward a single unit douching device which includes a flexible bag having an opening therein. A rigid nozzle is affixed to the bag at a location remote from the opening. A sealing means is also affixed to the bag adjacent the opening to seal the opening after douching materials are inserted through the opening into the bag.

U.S. Pat. No. 3,693,783, entitled "Vaginal Syringe Package Including A Supply Of Disposable Dispensing Containers And Integral Means For Storing Same" to Hart, illustrates a two-part housing that is small enough to be carried in a woman's handbag and which contains a plurality of compactly folded, disposable, concentrated-medicament-containing, thin-walled, flexible, limp plastic bags. The housing also contains a hollow elongated bone having a plurality of orifices at the distal end thereof. The concentrated medicament can dissolve or disperse in water. The housing further contains a viscous germicidal mass in which the bone is stored when not in use.

These prior art disclosures fail to teach a device including a highly portable dispenser having separate and distinct reservoirs to segregate a two-part chemical system until the desired time of use, and a combination applicator nozzle and blending manifold, wherein activation of the device fluidically couples the deformable chemical reservoirs, provides immediate intermixing of the two-part chemical system, and facilitates expulsion, under pressure, through at least one orifice, or alternatively a plurality of circumferentially spaced orifices, of the now blended chemical system within a body cavity.

SUMMARY OF THE INVENTION

The present invention is directed toward an applicator device useful for delivering an antimicrobial mixture to a body cavity. The applicator device includes a pair of deformable reservoirs for initial retention and segregation of each component of a two-part antimicrobial mixture. When it is desirable to expel the antimicrobial mixture into a body cavity, the deformable reservoirs are brought into fluidic communication with a manifold, wherein intermixing of the segregated components results in activation of the two-part antimicrobial mixture. Subsequent to intermixing, the now activated antimicrobial mixture flows from the manifold to a perforate applicator tip, from which it is expelled into the body cavity.

When pressure is brought to bear simultaneously upon each of the reservoirs, they both experience a change in volume between a non-deformed and a deformed state. The volume of antimicrobial mixture expelled through the applicator as a result of this simultaneous deformation defines a unit dosage of the antimicrobial mixture.

In an embodiment, the body cavity is intended to be the vagina of a human female and the antimicrobial mixture is intended to be a blend of hydrogen peroxide and acetic acid.

Accordingly, it is a primary objective of the instant invention to provide a device in the form of a highly portable dispenser, including separate and distinct reservoirs effective for segregating a two-part chemical system until the desired time of use, and containing a combination applicator nozzle and blending manifold. Activation of the device results in the fluidic coupling of the chemical reservoirs, and provides immediate intermixing of the two-part chemical system within the blending manifold thereby facilitating expulsion of the now blended and activated chemical system, under pressure, through a plurality of circumferentially spaced orifices, within a body cavity.

It is a further objective to provide such a device wherein the body cavity is the vaginal canal, and the two-part chemical system is effective for the treatment of bacterial vaginosis.

It is yet an additional objective of the instant invention to provide a two-part chemical system formed of acetic acid and hydrogen peroxide.

It is a still further objective to provide a kit designed to provide a highly portable means for treatment of bacterial vaginosis and like conditions leading to vaginal discomfort and/or discharge. The kit will include an applicator device useful for delivering an antimicrobial mixture to a body cavity, inclusive of a combination applicator nozzle and blending manifold constructed and arranged to be selectively placed in fluid communication with a pair of deformable reservoirs, which provide for the initial retention and segregation of each component of a two-part antimicrobial mixture. The kit will further contain a two-part chemical mixture whose components include acetic acid and hydrogen peroxide.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 1 illustrates an embodiment of the invention in a closed position;

FIG. 2 illustrates the embodiment of FIG. 1 in a partially opened position;

FIG. 3 illustrates the embodiment of FIG. 1 opened to a point where the fluid reservoirs are compressed so as to initiate flow through the nozzle;

FIG. 4 illustrates the embodiment of FIG. 1 opened to a point where the fluid reservoirs are depleted and flow through the nozzle has ceased;

FIGS. 6A, 6B, 6C, 6D and 6E illustrate the traversal of the blending manifold assembly, as the embodiment of FIG. 1 is opened causing the seal disrupting protuberances of the blending manifold assembly to pierce the bladder seals of each fluid reservoir simultaneously;

FIG. 6F is an exploded view of the blending manifold assembly as it relates to the manifold retaining body of the outer shell of the device;

FIG. 7 illustrates an alternative embodiment of the invention in a closed position;

FIG. 8 illustrates the embodiment of FIG. 7 in a partially opened position;

FIG. 9 illustrates the embodiment of FIG. 7 opened to a point where the fluid reservoirs are compressed so as to initiate flow through the nozzle;

FIG. 10 illustrates the embodiment of FIG. 7 opened to a point where the fluid reservoirs are depleted and flow through the nozzle has ceased;

FIGS. 13A, 13B, 13C and 13D respectively, illustrate the interaction between the cutting face and the bladder seal as the outer shells of the device are rotated about the blending manifold assembly wherein the bladder seals are ruptured;

FIGS. 13E, 13F, 13G and 13H provide a cut-away view of the interaction between the cutting face and the bladder seal, which parallel the positions of FIGS. 13A-13D respectively;

FIG. 14A is a close-up cutaway view of the embodiment of FIG. 7, which illustrates the fluidic pathway defined by the blending manifold assembly and the manifold retaining body circumscribed by the outer shells of the device;

FIG. 14B is a perspective view of the device positioned as in FIG. 14A;

FIG. 14C is a cross-sectional view of the device as depicted in FIG. 14B, as taken through line 14C-14C.

DETAILED DESCRIPTION OF THE INVENTION

Figure 5:
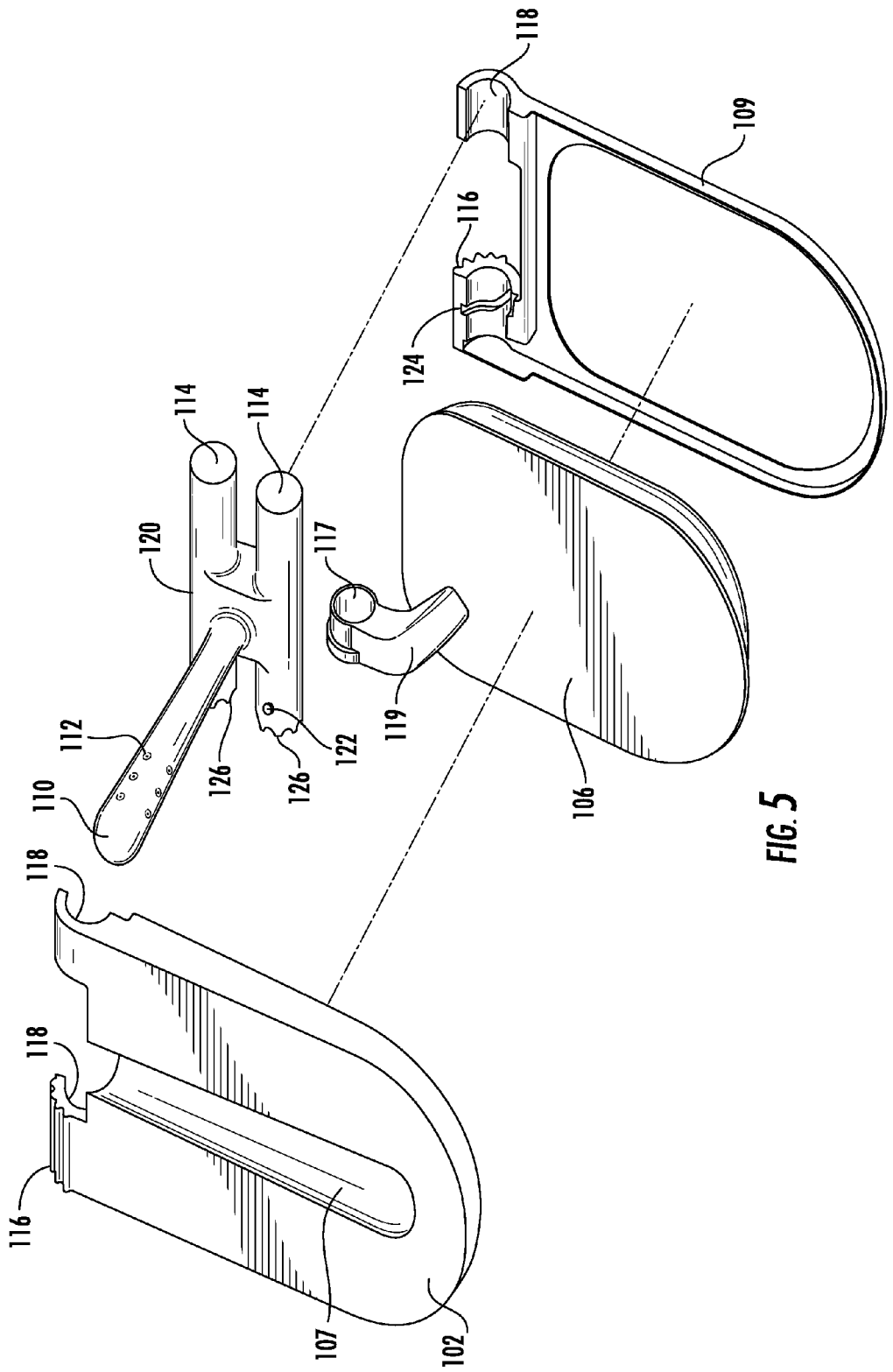
FIG. 5 illustrates an exploded view of portions of the embodiment of FIG. 1.

In a generic sense, it is the purpose of this invention to provide a device in the form of a highly portable dispenser, including separate and distinct deformable reservoirs effective for segregating a two-part chemical system until the desired time of use, and containing a combination applicator nozzle and blending manifold. Illustrative of materials useful for the reservoir are a plasticized foil, a low-density polyethylene or the like. Materials useful for the applicator nozzle are polymers such as polypropylene or polyethylene. These materials are merely illustrative, and not limiting. The invention contemplates the use of any suitable materials of construction.

In one particular embodiment, the invention will provide a kit inclusive of the device and a two-part chemical system including acetic acid and hydrogen peroxide.

In the illustrated, albeit non-limiting embodiments, the device is depicted as having a clam-shell like structure, wherein there are provided first and second halves, which are each designed to rotate about an axis defined by a blending manifold. Each half contains a sealed deformable reservoir filled with a distinct fluid, each respectively representing one part of a two-part chemical system. Initial rotation of each half about its axis, from an initial closed or storage position, to a semi-opened position, results in exposure of an applicator nozzle. The applicator nozzle may have at least one, and as illustrated, albeit not limited thereto, a plurality of orifices. The applicator nozzle is adapted for insertion within a body cavity. Upon further rotation of the first and second halves about their axes, the sealed reservoirs are breached causing them to become fluidically coupled with their respective blending manifold leg, which, in turn, is in fluid communication with the applicator nozzle. Via continued rotation, pressure is brought to bear upon the deformable reservoirs, forcing fluid therefrom, and subsequently through the blending manifold assembly, thereby facilitating intermixing of the two distinct fluids. This intermixing results in activation of the two-part chemical system. The continued application of pressure results in compression and deformation of the reservoirs, thereby facilitating expulsion of the now blended and activated chemical system, under pressure, through a plurality of circumferentially spaced orifices in the applicator nozzle, enabling effective treatment of the body cavity.

While the two-part chemical system can be any system designed to treat a body cavity, in an illustrative, albeit non-limiting embodiment, the system is a blend of acetic acid and hydrogen peroxide, formulated to enable normalization of pH levels and mitigation of bacterial vaginosis when instilled in a human vagina.

In order to show efficacy of the two-part chemical system, formed from acetic acid and hydrogen peroxide, for mitigating the effects of bacterial vaginosis, the following experiment was conducted.

The objective was to evaluate the response of patients complaining of vaginal discharge who received a vaginal rinse solution composed of hydrogen peroxide and acetic acid.

A total of 294 patients complaining of vaginal discharge were tested then treated with the combined hydrogen peroxide/acetic acid vaginal rinse then reevaluated for safety and effectiveness of treatment.

The results indicated that 82% of patients who received a combined hydrogen peroxide/acetic acid vaginal rinse experienced a positive therapeutic result for the complaint of vaginal discharge.

It was concluded that combined hydrogen peroxide/acetic acid vaginal rinsing provides a safe and effective low cost improvement to women with undesirable vaginal discharge.

METHODS AND MATERIALS 294 patients were seen in a private office setting over a 24-month period complaining of vaginal discharge. 92 of these patients also reported experiencing vaginal discomfort ranging from itching to a burning sensation. None of these patients were experiencing active vaginal bleeding nor did any have any visible lesions, ulcer, or abrasions, as they would have been excluded from the study. 40 of the patients were pregnant, 22 were in the third trimester and 18 were in the second trimester.

136 of the patients were white, 110 were Hispanic, and 48 were African American. 10 of these patients had been diagnosed with diabetes mellitus.

On the initial visit, patients underwent a speculum evaluation, vaginal pH testing and vaginal culture and sensitivity testing. This was followed by the insertion of 90 milliliters (3 ounces) of an aqueous solution consisting of 3% hydrogen peroxide and 5% acetic acid. The pH of the aqueous solution is 2.5. An ASEPTO syringe was used to introduce the solution.

The patients were then transferred to a consultation room and any questions were answered. The patients then filled out a short card commenting on the treatment and thereby provided collectible data. Patients then were given a follow up appointment in 7 to 10 days. During the follow up appointment the patients underwent a repeat speculum evaluation and pH determination. The results of their respective cultures were reviewed with the patients and if the cultures were positive, appropriate treatments were given. Following this second visit, the patient was given another questionnaire to comment on the treatment. Data was collected to obtain insight into safety, comfort, and response to treatment.

Of the 294 patients who presented with a chief complaint of vaginal discharge, 62 had a positive culture. Of these positive cultures, 30(48%) had bacterial vaginosis, 25(40%) had candida species, and 7(11%) had trichomonas vaginalis. Average pre-treatment vaginal pH was 5.1 at the first visit. Average post-treatment vaginal pH was 4.0.

Of the 294 patients, 12 reported that the treatment was uncomfortable. Of these 12 who reported that the treatment was uncomfortable, 2 described the discomfort as moderately uncomfortable and 10 described the discomfort as mildly uncomfortable.

None of the patients experienced appreciable erythema, swelling, or any signs suggestive of allergic reaction to the administration of the solution.

Of the 225 patients, which returned for their follow up visit, the average vaginal pH was 4.1. None of the patients reported any subsequent rash, irritation or any symptoms suggesting an allergic reaction to the application of the solution.

184 of the 225(82%) patients that were seen during the follow up visit described the treatment as helpful.

Vaginal discharge is a very common medical complaint, which accounts for a significant number of women seeking medical treatment. Causes of vaginal discharge include: normal physiologic variation, allergic reaction to spermicides and deodorants, vaginitis, and certain vaginal douches among others. Anything that alters the relatively low vaginal pH or negatively impacts the normally present *lactobacillus* species that inhabit the vaginal vault can contribute to the development of undesirable vaginal discharge. Of particular interest is the production of hydrogen peroxide by certain species of *lactobacilli*. Hydrogen peroxide has known antimicrobial properties, which kills bacteria and viruses.

Acetic acid in low concentrations has been used for decades by a number of women in different countries as a vaginal cleanser. By merely lowering the vaginal pH, the vaginal vault is less susceptible to pathogenic bacteria.

This study evaluated a combined product containing a mixture of hydrogen peroxide and acetic acid. The combined solution was introduced within the vagina to ascertain whether a positive clinical outcome could be attained. These two substances when combined in a physiologically compatible concentration were found to afford a positive physiological outcome in an ambulatory clinical setting. Cost of treatment was very acceptable and treatment benefit was immediate.

The instantly presented embodiments of the invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the present invention, as represented in the Figures, is not intended to limit the scope of the invention, as claimed, but is merely representative of presently preferred embodiments of the invention.

The series of figures numbered 1-4 and 7-10 respectively depict a representative activation of the respective embodiments shown therein, as the device is opened and activated. The first of the series of FIGS. (1 and 7) show the device in a closed or storage position. It is envisioned that the device may be provided in some type of protective wrap (not shown) that will be removed prior to use. The second figure in the series, (2 and 8) show the device opened to the extent that the hidden applicator tip has been exposed. The third FIGS. (3 and 9) illustrates the deformable reservoirs coming into contact with one another, whereupon the continuous application of pressure results in discharge of the now intermixed two-part chemical mixture from at least one orifice 112 in the applicator nozzle 110. The fourth FIGS. (4 and 10) illustrates the reservoirs having been completely collapsed, whereupon a prescribed dosage unit of the activated two-part chemical mixture has been expelled within the body cavity.

Now, with reference to FIG. 1, an embodiment of the invention 100, shown in an initial closed position, is illustrated. In this embodiment, the two halves of the device 100 are mirrored images of one another. First and second main body parts 102 and 104 form the basic structure. They each contain a formed depression 107 (see FIG. 2) designed to encase applicator nozzle 110 when the device is in its closed position. First and second outer shells 109 and 113 are designed to mate with the main body parts 102 and 104 and thereby encase first and second sealed reservoirs 106 and 111 there between. The first and second sealed reservoirs 106 and 111 each contain one part of a two-part chemical system. Engagement gears 116 are provided to assist in driving the blending manifold assembly 120 (FIG. 2). Each blending manifold leg 114 resides within the area of rotation formed by the joining of the main body parts 102,104 and outer shells 109,113, which thereby form a manifold retaining area, and the center thereof each respectively define the axis of rotation for their respective halves. Note that in the closed position, the right ends of each blending manifold leg 114 are initially even with the outer periphery of the device 100.

Referring to FIG. 2, the embodiment of FIG. 1 is shown in a partially opened position. Note that in this embodiment, as the rotation occurs, the blending manifold assembly 120 has begun to move from right to left so as to perforate the respective seals of the reservoirs 106,111 as will be more specifically illustrated in later figures.

FIG. 3 further illustrates the embodiment of FIG. 1 opened to a point where the fluid reservoirs 106,111 are compressed so as to initiate flow through the circumferentially spaced orifices 112, of applicator nozzle 110. The embodiment showing multiple orifices 112 is merely illustrative, and it is understood that the invention contemplates any number or positioning of orifices.

FIG. 4 illustrates the embodiment of FIG. 1 opened to a point where the fluid reservoirs 106,111 are depleted and flow through orifices 112 of the applicator nozzle 110 has ceased.

Now referring to FIG. 5, there is illustrated an exploded view of portions of the embodiment of FIG. 1. Main body part 102, having depression 107 for receiving applicator tip 110 when in a closed position is shown. Bearing surfaces 118, present on main body part 102 and outer shell 109 forms a receiving area for blending manifold assembly 120. The receiving area defines an axis that is concurrent with the axis of rotation of each half of the device. Elements 126 define at least one sharp protuberance designed to pierce reservoir bladder seals 117. Linking member 119 protrudes from reservoir 106 in order to provide fluid communication between the reservoir 106 and blending manifold assembly 120. As the two halves of the device 100 are rotated from their closed position, the blending manifold assembly 120 translates from right to left by virtue of guide pin 122 engaging guiding groove 124.

FIGS. 6A, 6B, 6C, 6D and 6E illustrate the traversal of the blending manifold assembly 120 as the embodiment of FIG. 1 is opened causing the at least one seal disrupting protuberances 126 of each blending manifold leg 114 to pierce the bladder seals 117 of each fluid reservoir simultaneously. It is noted that as one observes the positioning of the blending manifold assembly 120 going from FIG. 6A-6E, the movement of the ends of each blending manifold leg 114 relative to the main body of the device is readily apparent.

FIG. 6F is an exploded view of the blending manifold assembly 120 as it relates to the manifold retaining area defined by the outer shells of the device (see FIG. 2). It more clearly illustrates the interaction of the guide pin 122 and guiding groove 124.

FIG. 7 illustrates an alternative embodiment of the invention in an initial closed position. This embodiment is configured somewhat differently, so that both halves are identical, not mirror images. Main body parts 202 and 204 form the basic structure. They contain a formed depression 207 (see FIG. 8) designed to encase applicator nozzle 110 when the device is in its closed position. Outer shells 209 are designed to mate with the main body parts 202 and thereby encase deformable sealed reservoirs 206 there between. The structure of these reservoirs is identical, however each contains a different component of the two-part chemical system. The ends of each blending manifold leg 214 having a bearing surface 222 reside within the area of rotation formed by the joining of the main body parts 202 and outer shells 209, which define a manifold retaining area, wherein the center thereof each respectively define the axis of rotation for their respective halves.

FIG. 8 illustrates the embodiment of FIG. 7 in a partially opened position.

FIG. 9 illustrates the embodiment of FIG. 7 opened to a point where the fluid reservoirs 206 are compressed so as to initiate flow through at least one orifice 112 therein. The embodiment as illustrated, albeit non-limiting, illustrates a plurality of circumferentially spaced orifices 112 of the applicator nozzle 110.

FIG. 10 illustrates the embodiment of FIG. 7 opened to a point where the fluid reservoirs 206 are depleted and flow through the orifices 112 of applicator nozzle 110 has ceased.

Figure 11:
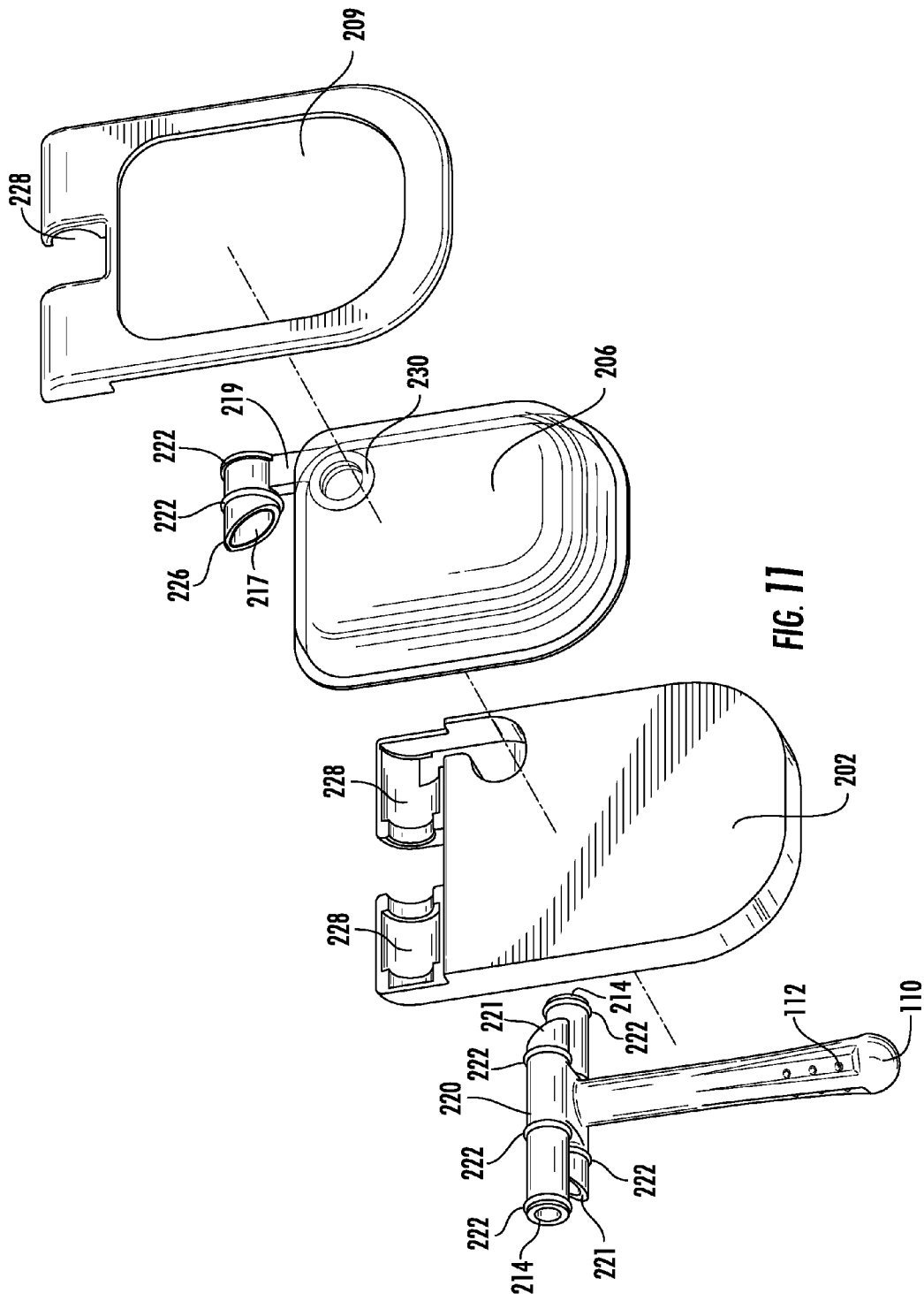
FIG. 11 illustrates an exploded view of portions of the embodiment of FIG. 2.

FIG. 11 illustrates an exploded view of portions of the embodiment of FIG. 2. Main body part 202 is shown. Bearing surfaces 228, present on main body part 202 and outer shell 209 form a receiving area for each blending manifold leg 214 of blending manifold assembly 220. The receiving area defines an axis that is concurrent with the axis of rotation of each half of the device. Blending manifold assembly cutting face 221 defines an obliquely angled cutting surface designed to align in parallel fashion with the reservoir bladder seal 217 so as to cut through the reservoir bladder seal 217 during rotation of the halves of the device. Linking member 219 protrudes from reservoir 206 in order to provide fluid communication between the reservoir 206 and blending manifold assembly 220. As the two halves of the device 200 are rotated from their closed position, the abutting and obliquely angled ends of both the blending manifold assembly cutting face 221 and reservoir sealing portion 226 rotate with respect to one another whereby the leading edge of the blending manifold assembly cutting face 221 cuts the reservoir bladder seal 217. Plural bearing surfaces 222 serve to maintain axial alignment of the device parts during rotation, and also form a liquid seal as required to direct fluid from the reservoirs 206 toward the blending manifold assembly 220 and subsequently toward the orifices 112 of the applicator nozzle 110. Element 230 illustrates a sealable filling port for the reservoirs 206. This sealing element is merely illustrative, as the present invention contemplates any manner of filling and sealing of the reservoirs 206 prior to their use.

Figure 12:
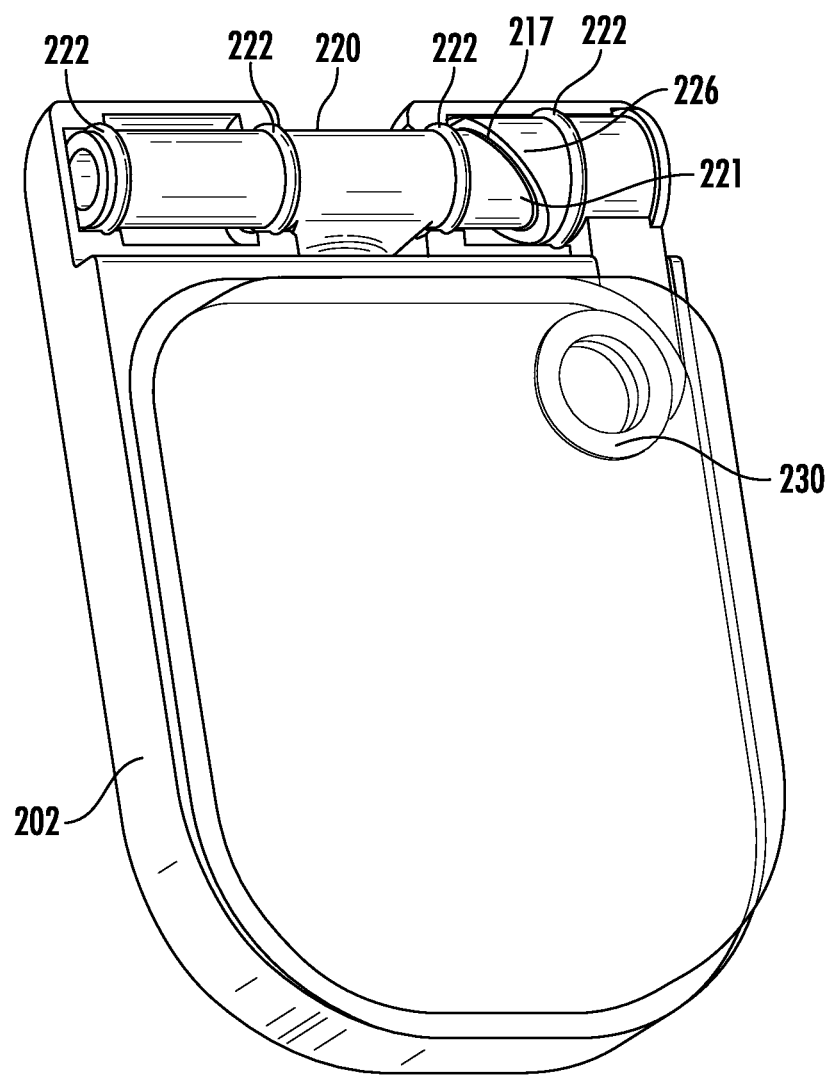
FIG. 12 illustrates the initial relationship of the obliquely abutted cutting face and bladder seal, as they are positioned within the manifold retaining body prior to opening of the embodiment of FIG. 7.

FIG. 12 illustrates an alternative view demonstrating the initial relationship of the obliquely abutted blending manifold assembly cutting face 221 and bladder seal 217, as they are positioned within the device prior to opening of the embodiment of FIG. 7.

FIGS. 13A, 13B, 13C and 13D respectively, illustrate the interaction between the cutting face 221 and the bladder seal 217 as the outer halves of the device 200 are rotated about the blending manifold assembly 220 wherein the bladder seals are ruptured;

FIGS. 13E, 13F, 13G and 13H provide a cut-away view of the interaction between the cutting face and the bladder seal, which parallel the positions of FIGS. 13A-13D respectively;

FIG. 14A is a close-up cutaway view of the embodiment of FIG. 7, taken along section line 14C-14C of FIG. 14B, which illustrates the fluidic pathway defined between each leg 214 of the blending manifold assembly 220 and the reservoirs 206 of the device. Pathway 232 shows flow from a first half of the device toward the outlet of the blending manifold assembly 220 into the throat of the applicator nozzle 110. Pathway 234 illustrates an equivalent pathway from the second half of the device.

FIG. 14B is a perspective view of the device positioned as in FIG. 14A.

FIG. 14C is a cross-sectional view of the device as depicted in FIG. 14B, as taken through line 14C-14C.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention that are obvious to those skilled in the art are intended to be within the scope of the following claims.

What is claimed is:

1. A device for dispensing a two-part chemical system to a body cavity comprising:
 a first half including a first sealed reservoir, containing a first part of a two-part chemical system, said reservoir encased between a first main body part and a first outer shell;
 a second half including a second sealed reservoir, containing a second part of a two-part chemical system, said reservoir encased between a second main body part and a second outer shell;

a blending manifold assembly having a first blending manifold leg and a second blending manifold leg; and an applicator nozzle in fluid communication with said blending manifold assembly having at least one orifice that is adapted to dispense said two-part chemical system within a body cavity;

each said first and second halves are constructed and arranged for rotation about an axis of rotation defined by said first blending manifold leg and said second blending manifold leg respectively;

whereby initial rotation of each said first and second halves about their respective axis of rotation brings each said sealed reservoir into fluid communication with each said respective manifold leg, and continued rotation of each said first and second halves about their respective axis of rotation causes each reservoir to respectively deliver said first and second parts of said two-part chemical system into said blending manifold assembly;

wherein said first and second parts of said two-part chemical system are mixed within said blending manifold assembly, and subsequently flow through said applicator nozzle and are adapted to be expelled into said body cavity via said at least one orifice.

2. The device of claim 1 wherein each said first and second manifold leg is provided with at least one protuberance constructed and arranged to pierce a reservoir bladder seal of each said respective sealed reservoir, whereby upon rotation of said halves of said device, each of said protuberances pierces each said respective reservoir bladder seal, thereby bringing each said sealed reservoir into fluid engagement with each said respective manifold leg.

3. The device of claim 1 wherein each said first and second manifold leg is provided with an obliquely angled cutting surface which is constructed and arranged to be positioned in a spaced parallel abutting alignment with a reservoir bladder seal of each said respective sealed reservoir, whereby upon rotation of said halves of said device, each obliquely angled cutting surface cuts each respective reservoir bladder seal, thereby bringing each said sealed reservoir into fluid engagement with each said respective manifold leg.

4. The device of claim 1 wherein said applicator nozzle is provided with a plurality of circumferentially spaced orifices.

5. The device of claim 1 wherein said body cavity is a vagina.

6. The device of claim 1 wherein said two-part chemical system includes acetic acid and hydrogen peroxide.

7. The device of claim 6 wherein said acetic acid is provided as a 5 percent solution and said hydrogen peroxide is provided as a 3 percent solution.

8. A kit for administering a two-part chemical system to a body cavity comprising:
a device having a first half including a first sealed reservoir, containing a first part of a two-part chemical system, said reservoir encased between a first main body part and a first outer shell;
a second half including a second sealed reservoir, containing a second part of a two-part chemical system, said reservoir encased between a second main body part and a second outer shell;
a blending manifold assembly having a first blending manifold leg and a second blending manifold leg; and
an applicator nozzle in fluid communication with said blending manifold assembly having at least one orifice that is adapted to dispense said two-part chemical system within a body cavity;

each said first and second halves being constructed and arranged for rotation about an axis of rotation defined by said first blending manifold leg and said second blending manifold leg respectively;

whereby initial rotation of each said first and second halves about their respective axis of rotation brings each said sealed reservoir into fluid communication with each said respective manifold leg, and continued rotation of each said first and second halves about their respective axis of rotation causes each reservoir to respectively deliver said first and second parts of said two-part chemical system into said blending manifold assembly;

wherein said first and second parts of said two-part chemical system are mixed within said manifold assembly, and subsequently flow through said applicator nozzle and are adapted to be expelled into said body cavity via said at least one orifice.

9. The kit of claim 8, wherein said applicator nozzle is provided with a plurality of circumferentially spaced orifices.

10. The kit of claim 8 wherein said two-part chemical system includes acetic acid and hydrogen peroxide.

11. The kit of claim 10 wherein said acetic acid is provided as a 5 percent solution and said hydrogen peroxide is provided as a 3 percent solution.

12. A kit for the treatment of bacterial vaginosis and vaginal discharge comprising:
a device having a first half including a first sealed reservoir, containing a first part of a two-part chemical system, said reservoir encased between a first main body part and a first outer shell;
a second half including a second sealed reservoir, containing a second part of a two-part chemical system, said reservoir encased between a second main body part and a second outer shell;
a blending manifold assembly having a first blending manifold leg and a second blending manifold leg; and
an applicator nozzle in fluid communication with said blending manifold assembly having at least one orifice that is adapted to dispense said two-part chemical system within a vagina;
each said first and second halves are constructed and arranged for rotation about an axis of rotation defined by said first blending manifold leg and said second blending manifold leg respectively;
whereby initial rotation of each said first and second halves about their respective axis of rotation brings each said sealed reservoir into fluid communication with each said respective manifold leg, and continued rotation of each said first and second halves about their respective axis of rotation causes each reservoir to respectively deliver said first and second parts of said two-part chemical system into said blending manifold assembly;
wherein said first and second parts of said two-part chemical system are mixed within said manifold assembly, and subsequently flow through said applicator nozzle and are adapted to be expelled into said vagina via said at least one orifice.

13. The kit of claim 12, wherein said applicator nozzle is provided with a plurality of circumferentially spaced orifices.

14. The kit of claim 12 wherein said two-part chemical system includes acetic acid and hydrogen peroxide.

15. The kit of claim 14 wherein said acetic acid is provided as a 5 percent solution and said hydrogen peroxide is provided as a 3 percent solution.

* * * * *